US011229410B2

(12) United States Patent
Turner et al.

(10) Patent No.: US 11,229,410 B2
(45) Date of Patent: Jan. 25, 2022

(54) SYSTEMS AND METHODS TO CONTROL RADIATION SCANNER POSITIONING

(71) Applicant: Illinois Tool Works Inc., Glenview, IL (US)

(72) Inventors: Jackson Turner, Plymouth, MN (US); Joseph Schlecht, Edina, MN (US)

(73) Assignee: Illinois Tool Works Inc., Glenview, IL (US)

( * ) Notice: Subject to any disclaimer, the term of this patent is extended or adjusted under 35 U.S.C. 154(b) by 25 days.

(21) Appl. No.: 16/895,767

(22) Filed: Jun. 8, 2020

(65) Prior Publication Data

US 2021/0378606 A1 Dec. 9, 2021

(51) Int. Cl.
*A61B 6/00* (2006.01)
*A61B 6/04* (2006.01)
*A61B 6/06* (2006.01)

(52) U.S. Cl.
CPC .................. *A61B 6/04* (2013.01); *A61B 6/06* (2013.01); *A61B 6/4458* (2013.01); *A61B 6/466* (2013.01); *A61B 6/54* (2013.01)

(58) Field of Classification Search
CPC ........... A61B 6/545; A61B 6/547; A61B 6/54; A61B 6/4441; A61B 6/465; A61B 6/467
See application file for complete search history.

(56) References Cited

U.S. PATENT DOCUMENTS

| 2016/0220219 | A1* | 8/2016 | Lalena | A61B 6/467 |
| 2016/0235386 | A1* | 8/2016 | Schweizer | A61B 6/4476 |
| 2017/0347979 | A1 | 12/2017 | Fehre | |
| 2019/0261932 | A1 | 8/2019 | Divoky | |
| 2019/0311490 | A1 | 10/2019 | Crawford | |

OTHER PUBLICATIONS

Int'l Search Report and Written Opinion Appln No. PCT/US2021/033602 dated Sep. 8, 2021.

* cited by examiner

*Primary Examiner* — Don K Wong
(74) *Attorney, Agent, or Firm* — McAndrews, Held & Malloy, Ltd.

(57) ABSTRACT

An example scanner positioning control system includes: a display; a processor; and a computer readable storage medium comprising computer readable instructions which, when executed, cause the processor to: output, via the display, a first visual representation of an arrangement of a radiation source, a radiation detector, and a workpiece positioner; identify a change to be made to the arrangement of at least one of the radiation source, the radiation detector, or the workpiece positioner; output, via the display, a second visual representation of the arrangement of the radiation source, the radiation detector, and the workpiece positioner based on the change to be made to the arrangement; and control a scanner positioning system to physically move the at least one of the radiation source, the radiation detector, and the workpiece positioner based on the change.

20 Claims, 8 Drawing Sheets

SYSTEMS AND METHODS TO CONTROL RADIATION SCANNER POSITIONING

BACKGROUND

This disclosure relates generally to radiography and, more particularly, to systems and methods to control radiation scanner positioning.

X-ray scanning systems involve directing high-intensity radiation toward a device or object under test to obtain one or more images that may not be obtainable using other scanning systems (e.g., ultrasound, visible light, etc.). X-ray scanning systems may have multiple parameters that are dependent on the relative arrangements of the components in the X-ray scanning system.

SUMMARY

Systems and methods to control radiation scanner positioning are disclosed, substantially as illustrated by and described in connection with at least one of the figures, as set forth more completely in the claims.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

The figures are not necessarily to scale. Wherever appropriate, similar or identical reference numerals are used to refer to similar or identical components.

DETAILED DESCRIPTION

Figure 1:
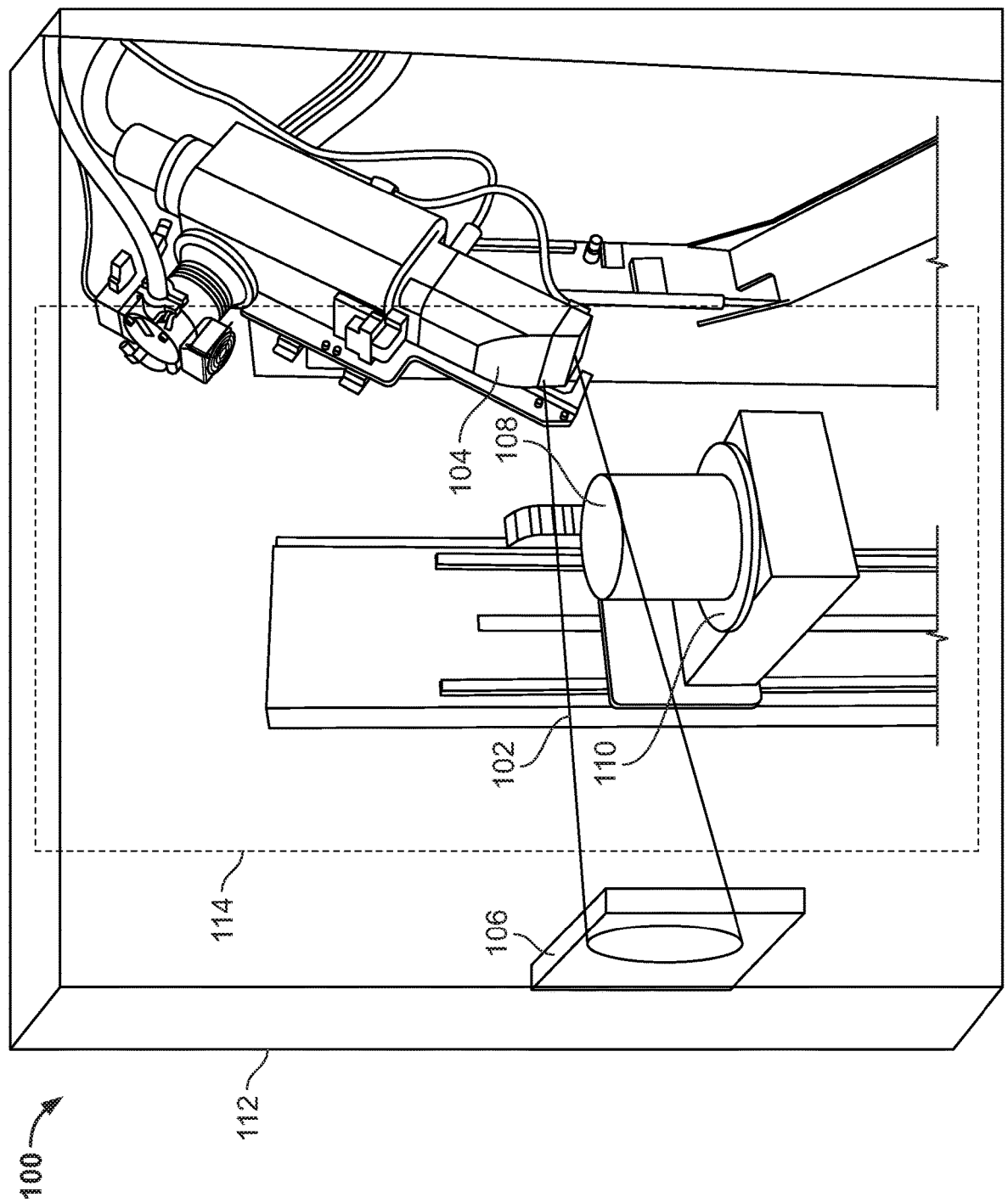
FIG. 1 illustrates an example X-ray scanning system that may be controlled using a scanner positioning control system, in accordance with aspects of this disclosure.

Conventional scanner positioning systems involve a user interface that provides controls for individual modes of component positioning. For instance, a conventional scanner positioning system may include a number and a range representative of the height of the X-ray emitter, a number and a range representative of the height of the manipulator, and/or a number and a range representative of the height of the X-ray receiver. However, the person operating the controls may not have a clear idea of the final position resulting from a change to the number on the interface. Accordingly, conventional scanner positioning systems may involve significant trial-and-error on the part of the operator to determine the desired positioning to achieve the desired scan.

Disclosed scanner positioning control systems and methods provide a significantly easier interface that enables an operator to see the proposed changes to an arrangement of the X-ray emitter, the manipulator, the X-ray detector, and/or any other components of the scanning system, prior to implementing the changes in the scanning system. In some examples, the scanner positioning control systems and methods provide visualizations of both the starting position prior to a positioning adjustment and the ending position following the positioning adjustment. In some examples, the scanner positioning control systems and methods may calculate and display relevant metrics, such as numeric measurements of distances between components and/or other measurements of position, calculated focal length and/or unsharpness parameters, and/or any other information. As a result, the operator may manipulate the virtual representations of the components via the interface until the desired arrangement or positioning is achieved, at which time the operator may command the scanner positioning control system to implement the changes via the appropriate actuators of the scanning system.

Disclosed example scanner positioning control systems include: a display; a processor; and a computer readable storage medium comprising computer readable instructions which, when executed, cause the processor to: output, via the display, a first visual representation of an arrangement of a radiation source, a radiation detector, and a workpiece positioner; identify a change to be made to the arrangement of at least one of the radiation source, the radiation detector, or the workpiece positioner; output, via the display, a second visual representation of the arrangement of the radiation source, the radiation detector, and the workpiece positioner based on the change to be made to the arrangement; and control a scanner positioning system to physically move the at least one of the radiation source, the radiation detector, and the workpiece positioner based on the change.

In some example scanner positioning control systems, the first visual representation includes at least one of: a projection of a current position of the radiation source onto a reference plane; a projection of a current position of the radiation detector onto the reference plane; a projection of a current position of the workpiece positioner onto the reference plane; or a projection of a part positioned on the workpiece positioner onto the radiation detector based on the current position of the radiation source, the radiation detector, and the workpiece positioner. In some example scanner positioning control systems, the second visual representation includes at least one of: a projection of a changed position of the radiation source onto the reference plane based on the change to be made to the arrangement; a projection of a changed position of the radiation detector onto the reference plane based on the change to be made to the arrangement; a projection of a changed position of the workpiece positioner onto the reference plane based on the change to be made to the arrangement; or a projection of the part positioned on the workpiece positioner onto the radiation detector based on the change to be made to the arrangement.

In some example scanner positioning control systems, the computer readable instructions cause the processor to control the scanner positioning system by controlling at least one of: an enclosure in which the radiation source, the radiation detector, and the workpiece positioner are enclosed; a door of the enclosure; boundaries of the enclosure; a limit of motion of at least one of radiation source, the radiation detector, or the workpiece positioner; a range of motion in which a collision involving at least one of radiation source, the radiation detector, or the workpiece positioner has less than a threshold likelihood of occurring; a filter wheel; a collimator; or a shutter.

In some example scanner positioning control systems, the computer readable instructions cause the processor to access current positions of the radiation source, the radiation detector, and the workpiece positioner, and determine the first visual representation of the arrangement of the radiation source, the radiation detector, and the workpiece positioner based on the positions. In some example scanner positioning control systems, the first visual representation includes at least one of a representation of a current focal point of radiation emitted by the radiation source or an updated focal point based on the change to be made to the arrangement. In some example scanner positioning control systems, the computer readable instructions cause the processor to determine at least one of a magnification, an unsharpness parameter, or a focal length of the radiation detector following the change to be made to the arrangement.

In some example scanner positioning control systems, the computer readable instructions cause the processor to: identify a trajectory to be followed by at least one of the radiation source, the radiation detector, or the workpiece positioner during a scanning operation, the trajectory having a starting arrangement of the radiation source, the radiation detector, and the workpiece positioner and an ending arrangement of the radiation source, the radiation detector, and the workpiece positioner; output, via the display, a third visual representation comprising the starting arrangement and the ending arrangement; and control the scanner positioning system during the scanning operation to physically move the at least one of the radiation source, the radiation detector, and the workpiece positioner based on the trajectory from the starting arrangement to the ending arrangement. In some example scanner positioning control systems, the third visual representation visually represents at least one of a change in position or a change in orientation of at least one of the radiation source, the radiation detector, and the workpiece positioner between the starting arrangement and the ending arrangement. In some example scanner positioning control systems, the first visual representation and the second visual representation are three-dimensional representations.

In some example scanner positioning control systems, the computer readable instructions cause the processor to determine a range of motion of at least one of the radiation source, the radiation detector, or the workpiece positioner, wherein at least one of the first visual representation or the second visual representation include a representation of the range. In some example scanner positioning control systems, the computer readable instructions cause the processor to determine whether a motion associated with the change to the arrangement will cause at least one of the radiation source, the radiation detector, or the workpiece positioner to exceed the limits of the range of motion.

In some example scanner positioning control systems, at least one of the first visual representation or the second visual representation includes a representation of a workpiece held on the workpiece positioner. In some example scanner positioning control systems, at least one of the first visual representation or the second visual representation includes a representation of a robot arm, an origin point of a movement of the workpiece positioner, or one or more vectors representative of the change to the arrangement. In some example scanner positioning control systems, the computer readable instructions are to cause the processor to output, via the display, a third visual representation of an intermediate arrangement of the radiation source, the radiation detector, and the workpiece positioner based on the arrangement and the change to be made to the arrangement.

In some example scanner positioning control systems, at least one of the first visual representation or the second visual representation includes at least one of an enclosure, an enclosure door, a filter wheel, a radiation source collimator, or a radiation source shutter. In some example scanner positioning control systems, the computer readable instructions cause the processor to determine at least one of a magnification, an unsharpness parameter, or a focal length of the radiation detector of the arrangement. Some example scanner positioning control systems include a user input device, wherein the computer readable instructions cause the processor to identify the change to be made to the arrangement based on one or more inputs via the user input device.

Some other disclosed example scanner positioning systems include: a display; a processor; and a computer readable storage medium comprising computer readable instructions which, when executed, cause the processor to: render a three-dimensional representation of a radiation source, a radiation detector, and a workpiece positioner based on an arrangement of the radiation source, the radiation detector, and the workpiece positioner; render changes to the arrangement in response to commands to change the arrangement; and control positions and orientations of the radiation source, the radiation detector, and the workpiece positioner based on the rendered arrangement including the rendered changes.

Still other disclosed example scanner positioning control systems include: a display; a processor; and a computer readable storage medium comprising computer readable instructions which, when executed, cause the processor to: output, via the display, a first visual representation of a first state of a radiation source, a radiation detector, and a workpiece positioner; identify a change to be made to the first state based on a modeled manipulation of the first visual representation; output, via the display, a second visual representation of a second state of the radiation source, the radiation detector reflecting the modeled manipulation; and control a scanner positioning system to physically move the at least one of the radiation source, the radiation detector, and the workpiece positioner to positions represented in the second state.

FIG. 1 illustrates an example X-ray scanning system 100 that may be controlled using a scanner positioning control system. The example X-ray scanning system 100 may be used to perform non-destructive testing (NDT) and/or any other scanning application. The example X-ray scanning system 100 is configured to direct X-rays 102 from an X-ray emitter 104 to an X-ray detector 106 through a workpiece 108 (e.g., an object under test). In the example of FIG. 1, a workpiece positioner 110 holds or secures the workpiece 108, and moves and/or rotates the workpiece 108 such that the desired portion and/or orientation of the workpiece 108 is located in the path of the X-ray radiation 102.

As discussed in more detail below, any of the X-ray emitter 104, the X-ray detector 106, and/or the workpiece positioner 110 may be positioned and/or reoriented using one or more actuators. Relative repositioning of the X-ray emitter 104, the X-ray detector 106, and/or the workpiece positioner 110 may result in different effects, such as changing the focal length, changing the focal point, changing an unsharpness parameter, changing a magnification (e.g., a ratio of distance between X-ray emitter and X-ray detector to distance between X-ray emitter workpiece positioner or to workpiece), changing a portion of the workpiece 108 that is scanned, and/or other effects.

The X-ray scanning system 100 further includes an enclosure 112, in which the X-ray emitter 104, the X-ray detector 106, and the workpiece positioner 110 are enclosed. The enclosure 112 includes one or more doors 114 or other access openings to, for example, insert or remove the workpiece 108, perform servicing on any of the components within the enclosure 112, and/or otherwise access an interior of the enclosure 112.

The X-ray detector 106 of FIG. 1 generates digital images based on incident X-ray radiation (e.g., generated by the X-ray emitter 104 and directed toward the X-ray detector 106). The example X-ray detector 106 may include a fluoroscopy detection system and a digital image sensor configured to receive an image indirectly via scintillation, and/or may be implemented using a sensor panel (e.g., a CCD panel, a CMOS panel, etc.) configured to receive the X-rays directly, and to generate the digital images. In other examples, the X-ray detector 106 may use a solid state panel coupled to a scintillation screen and having pixels that correspond to portions of the scintillation screen. Example solid state panels may include CMOS X-ray panels and/or CCD X-ray panels.

Example implementations of the workpiece positioner 110 include a mechanical manipulator, such a platen having linear and/or rotational actuators. Other example workpiece positioners 110 may include robotic manipulators, such as robotic arms having 6 degrees of freedom (DOF).

While the example of FIG. 1 includes an X-ray emitter 104 and an X-ray detector 106, in other examples the scanning system 100 may perform scanning using radiation in other wavelengths.

Figure 2:
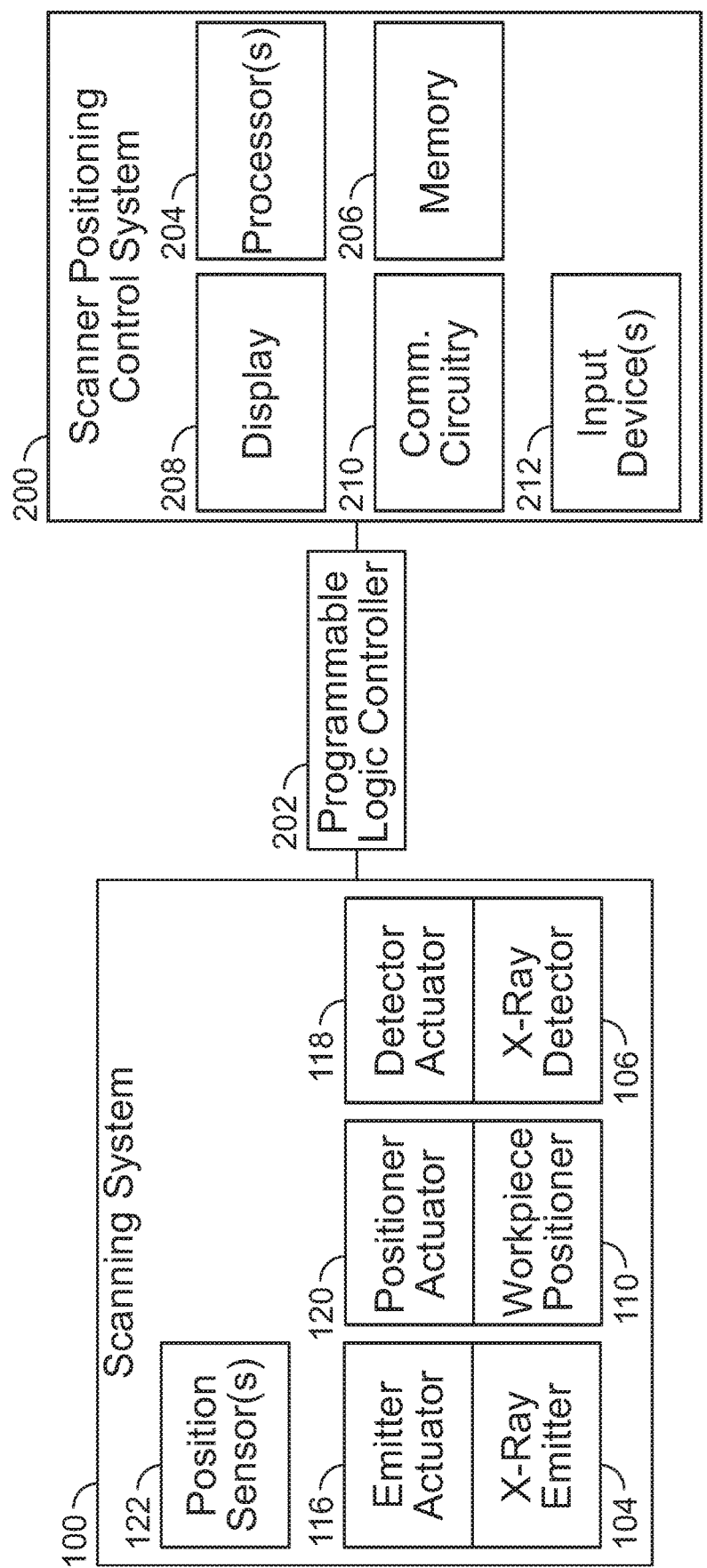
FIG. 2 is a block diagram of the example X-ray scanning system and scanning positioning control system of FIG. 1.

FIG. 2 is a block diagram of the example X-ray scanning system 100 of FIG. 1 and a scanning positioning control system 200. As discussed above, the example X-ray scanning system 100 includes an X-ray emitter 104, an X-ray detector 106, a workpiece positioner 110. The example X-ray scanning system 100 further includes a source actuator 116, a detector actuator 118, and a positioner actuator 120.

The X-ray scanning system 100 of FIG. 2 is communicatively coupled to the scanner positioning control system 200. In some examples, a programmable logic controller (PLC) 202 or other interface device may couple the scanner positioning control system 200 to the X-ray scanning system 100. For example, the PLC 202 may enable a personal computer or other generic computing device to communicate with (e.g., command, obtain information from) the actuators 116-120 and/or sensor(s) of the scanning system 100.

The example scanner positioning control system 200 of FIG. 2 includes one or more processor(s) 204, memory 206 and/or other computer readable storage device(s), a display 208, communication circuitry 210, and one or more input device(s) 212. The scanner positioning control system 200 controls positioning of the X-ray emitter 104 (e.g., via the source actuator 116), positioning of the X-ray detector 106 (e.g., via the detector actuator 118), and/or positioning of the workpiece positioner 110 and/or the workpiece 108 (e.g., via the positioner actuator 120. To reduce the trial-and-error involved in positioning the components 104-110, the example scanner positioning control system 200 outputs, via the display 208, visual representations of both a current arrangement of the X-ray emitter 104, the X-ray detector 106, and the workpiece positioner 110, and an updated arrangement of the X-ray emitter 104, the X-ray detector 106, and the workpiece positioner 110 based on manipulations of the arrangement made by the operator (e.g., via the input device(s) 212). Example operator input device(s) 212 include buttons, switches, analog joysticks, thumbpads, trackball s, and/or any other type of user input device.

The scanner positioning control system 200 controls the X-ray emitter 104, receives digital images from the X-ray detector 106, and/or outputs the digital images to the display device 208. Additionally or alternatively, the scanner positioning control system 200 may store digital images to a storage device. The scanner positioning control system 200 may output the digital images as digital video to aid in real-time non-destructive testing and/or store digital still images.

Figure 3:
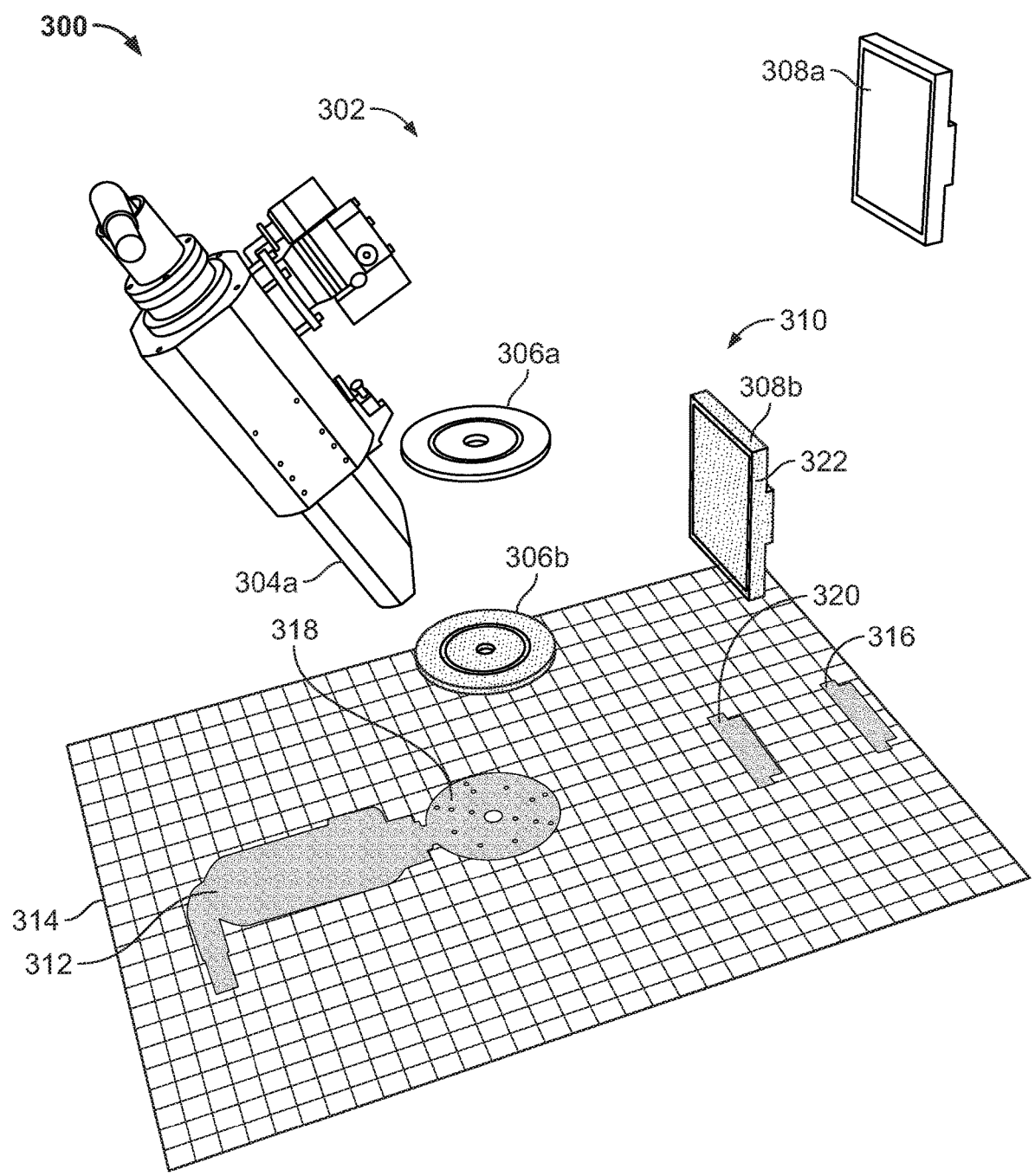
FIG. 3 illustrates an example interface that may be used to implement the scanner positioning control system, showing a first visual representation of a current arrangement of one or more components of the X-ray scanning system and a second arrangement representative of a change to the current arrangement of the one or more components.

In the example of FIG. 2, the scanner positioning control system 200 displays a three-dimensional representation of the current arrangement and the updated arrangement. FIG. 3 illustrates an example interface 300 that may be used to implement the scanner positioning control system 200, showing a first visual representation of a current arrangement 302 of components 304a, 306a, 308a of the X-ray scanning system 100, and a second arrangement 310 (e.g., updated components 306b, 308b) representative of a change to the current arrangement 302 of the components 304a-308a.

Using the input device(s) 212, the example scanner positioning control system 200 may identify change(s) to be made to the current arrangement (e.g., position(s) and/or orientation(s)) of at least one of the X-ray emitter 104, the workpiece positioner 110, and/or the X-ray detector 106. Based on the change(s) to the current arrangement 302 identified via the input device(s) 212, the scanner positioning control system 200 displays the visual representation of the updated arrangement. The example interface 300 may be manipulated (e.g., via the input device(s) 212) to change the positions and/or orientations of the components 304a, 306a, 308a and/or the viewpoint angle of the interface 300 (e.g., a camera angle, from which the arrangements 302, 310 are viewed on the interface 300). As the operator manipulates the position and/or orientation of one or more of the component(s) 304a, 306a, 308a, the scanner positioning control system 200 may generate a corresponding modified component and/or change the position of the modified component while maintaining the same position and/or orientation of the component(s) 304*a*, 306*a*, 308*a* in the current arrangement 302.

In an operational example, the operator may manipulate a cursor or other input device 212 to move the workpiece positioner 110 (e.g., the component 306*a*) on the interface 300. For example, the operator may click-and-drag the component 306*a* in the interface 300 to adjust the position and/or orientation, which is reflected by creation, positioning, and orienting of the updated component 306*b* on the interface 300. In the illustrated example of FIG. 3, the component 306*a* represents the current position of the workpiece positioner 110 and remains in the same position and orientation, while the updated component 306*b* represents changes to be made to the position and/or orientation of the workpiece positioner 110. The operator may repeatedly adjust the position and/or orientation of the updated component 306*b* until the desired position and/or orientation is achieved. When the desired positioning of the component 306*b*. Similarly, the operator may reposition and/or reorient the X-ray detector 106 in the interface by clicking-and-dragging the component 308*a* to adjust a position and/or orientation, which is represented by an updated component 308*b*.

The scanner positioning control system 200 further controls a scanner positioning system (e.g., the actuators 116, 118, 120, via the PLC 202) to physically move the X-ray emitter 104, the X-ray detector 106, and the workpiece positioner 110 based on the change represented by the updated arrangement 310. When a desired arrangement of the components 304*a*, 306*a*, 308*a* and/or updated components 304*b*, 306*b*, 308*b* is obtained via the interface 300, the operator commands the scanner positioning control system 200 to move the X-ray emitter 104, the X-ray detector 106, and the workpiece positioner 110 (e.g., via the PLC 202). In response to a command to implement the changed positions, the processor(s) 204 calculate paths between the positions of the components 304*a*, 306*a* 308*a* in the current arrangement 302 and the positions of the updated components 306*b*, 308*b* in the updated arrangement 310. The processor(s) 204 then command the source actuator 116, the detector actuator 118, and/or the positioner actuator 120 to move the X-ray emitter 104, the X-ray detector 106, and the workpiece positioner 110 (e.g., via the PLC 202). In some examples, the PLC 202 may calculate the paths based on coordinate information communicated by the scanner positioning control system 200.

To aid the operator in determining the desired positions of the X-ray emitter 104, the X-ray detector 106, and/or the workpiece positioner 110, the example scanner positioning control system 200 may include additional visual representations on the interface 300, such as a projection 312 of a current position of the X-ray emitter component 304*a* onto a reference plane 314; a projection 316 of a current position of the X-ray detector component 308*a* onto the reference plane 314; a projection 318 of a current position of the workpiece positioner component 306*a* onto the reference plane 314; a projection of a changed position of the X-ray emitter component 304*a* onto the reference plane 314 based on the change(s) to be made to the arrangement 302; a projection 320 of a changed position of the X-ray detector component 308*b* onto the reference plane 314 based on the change(s) to be made to the arrangement 302; a projection of a changed position of the workpiece positioner component 306*b* onto the reference plane 314 based on the change(s) to be made to the arrangement 302. Additionally or alternatively, the scanner positioning control system 200 may calculate and project a focal point 322 of the X-ray beam onto the current position of the X-ray detector component 308*a* and/or onto the updated position of the X-ray detector component 308*b*.

The example reference plane 314, and/or one or more other reference planes, assists the operator by displaying the relative current positions of the components 304*a*, 306*a*, 308*a* and/or the relative updated positions of the components 306*b*, 308*b* in a particular plane that may be difficult for the operator to precisely perceive spatial relationships between the components.

Additionally or alternatively, the example scanner positioning control system 200 may include visual representations on the interface 300 to project the part onto the X-ray detector to visualize the scan. Example visualizations may include a projection of a part positioned on the workpiece positioner component 306*a* onto the X-ray detector component 308*a* based on the current arrangement, and/or a projection of the part positioned on the workpiece positioner component 306*b* onto the X-ray detector component based on the change(s) to be made to the arrangement 302. To generate the projection, the example scanner positioning control system 200 may use graphics processing to determine the occlusion of the emitted X-rays from the current position of the X-ray emitter component 304*a* (which may be based on a determined collimator, energy level, and/or any other aspects of the X-ray emitter) by a workpiece positioned on the workpiece positioner component 306*a*, 306*b*. The workpiece may be rendered in the interface 300 from a 3D model of the workpiece and based on the current or changed position of the workpiece positioner component 306*a*, 306*b*.

In addition to the X-ray emitter component, the X-ray detector component, the workpiece positioner component, and/or the workpiece, the example scanner positioning control system 200 may include in the visual representations any of the door 114 of the enclosure 112, boundaries of the enclosure 112, limits of motion of the components 304*a*, 306*a*, 308*a*, ranges of motion of the components 304*a*, 306*a*, 308*a* in which a collision has less than a threshold likelihood of occurring, a filter wheel, collimators, shutters, and/or any other elements that may be movable and/or affect the position and/or orientation of the components 304*a*, 306*a*, 308*a*.

The example scanner positioning control system 200 may access current positions of the X-ray emitter 104, the X-ray detector 106, and/or the workpiece positioner 110 to determine the first visual representation of the arrangement of the radiation source, the X-ray emitter 104, the X-ray detector 106, and/or the workpiece positioner 110 based on the positions. To determine the current arrangement 302 (e.g., the positions of the X-ray emitter 104, the X-ray detector 106, and the workpiece positioner 110), the example scanning system 100 may include position sensor(s) 122 that determine the positions of the X-ray emitter 104, the X-ray detector 106, and the workpiece positioner 110, and communicate the positions to the scanner positioning control system 200 (e.g., via the PLC 202). The scanner positioning control system 200 may store a three-dimensional coordinate system including ranges of positions within which each of the X-ray emitter 104, the X-ray detector 106, and the workpiece positioner 110 may be located. Using the position information received from the position sensor(s) 122, the scanner positioning control system 200 determines the positions of the X-ray emitter 104, the X-ray detector 106, and the workpiece positioner 110, and/or the positions of any other component(s), within the coordinate system or reference frame defined by the interface 300.

As an example, the X-ray emitter 104 may be controlled using a linear actuator. The scanner positioning control system 200 may store a calibrated range of positions of the X-ray emitter 104 that correspond to the coordinate system. The position sensor(s) 122 may output a numerical value of the position of the X-ray emitter 104 along the length of the range of the linear actuator, such that the scanner positioning control system 200 may translate the sensed position of the X-ray emitter to the coordinate system in the interface 300. By storing similar position ranges with respect to the coordinate system, the scanner positioning control system 200 may determine the respective positions of the X-ray emitter 104, the X-ray detector 106, and the workpiece positioner 110, and translate the positions to present the current arrangement 302 in the interface 300.

The detected positions may further be used to determine and display secondary information, such as the projections on the reference plane 314, projections of the X-rays and/or the workpiece on the X-ray detector component 308a, X-ray detector focal length, a magnification level (e.g., zoom), an unsharpness parameter, and/or any other information that may be derived from the current positions of the X-ray emitter 104, the X-ray detector 106, and the workpiece positioner 110.

While the above example refers to a linear actuator, any other type(s) of actuator(s) or manipulator(s) may be used to physical position and/or manipulate the X-ray emitter 104, the X-ray detector 106, the workpiece positioner 110, the workpiece, and/or any other components. For example, the actuator(s) 116, 118, 120 may include 6 degree-of-freedom robot manipulators, rotational actuators (e.g., direct rotation, worm gear rotation, etc.), and/or any other type of actuator.

Figure 4:
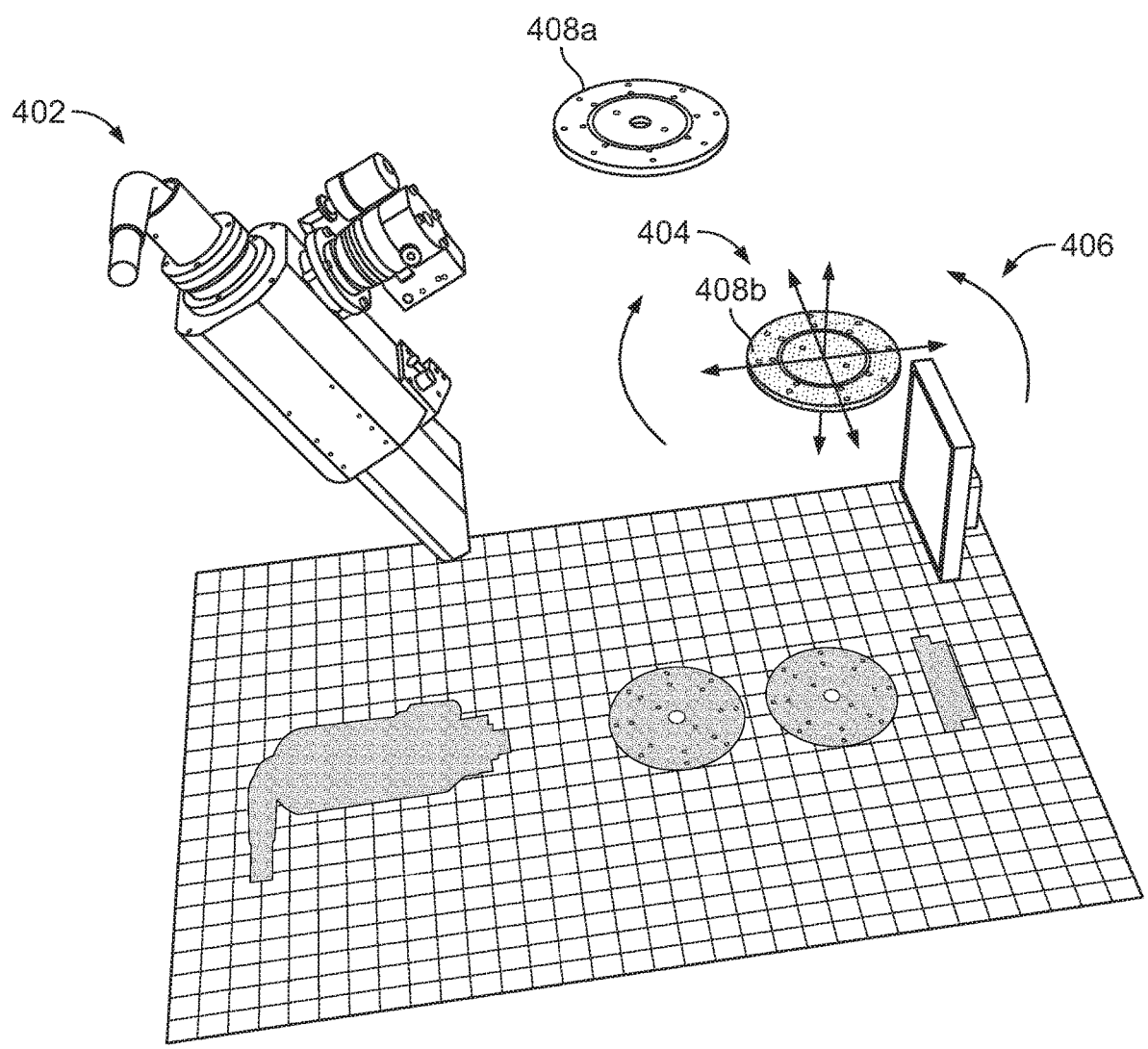
FIG. 4 illustrates an example interface that may be used to implement the scanner positioning control system, showing a first visual representation of a current arrangement of one or more components of the X-ray scanning system, a second arrangement representative of a change to the current arrangement of the one or more components, and an example guide graphic that may be used to define a change in position and/or orientation of the workpiece positioner.

FIG. 4 illustrates an example interface 400 that may be used to implement the scanner positioning control system 200, showing a first visual representation of a current arrangement 402 of one or more components of the X-ray scanning system 100, a second visual representation of an updated arrangement 404 representative of a change to the current arrangement 402 of the one or more components, and an example guide graphic 406 that may be used to define a change in position and/or orientation of the workpiece positioner 110.

In the example of FIG. 4, the scanner positioning control system 200 displays a current position of the workpiece positioner component 408a and an updated position of the workpiece positioner component 408b based on a change to the position of the workpiece positioner component 408b. Proximate to the updated workpiece positioner component 408b, the scanner positioning control system 200 displays the guide graphics 406 to enable the user to easily identified permitted modifications to the position and orientation of the workpiece positioner component 408b. The example guide graphics 406 in FIG. 4 illustrate translation guides (e.g., in an X-direction, a Y-direction, and a Z-direction), and rotation graphics (e.g., clockwise rotation and counterclockwise rotation in the plane of the workpiece positioner component 408b).

Figure 5:
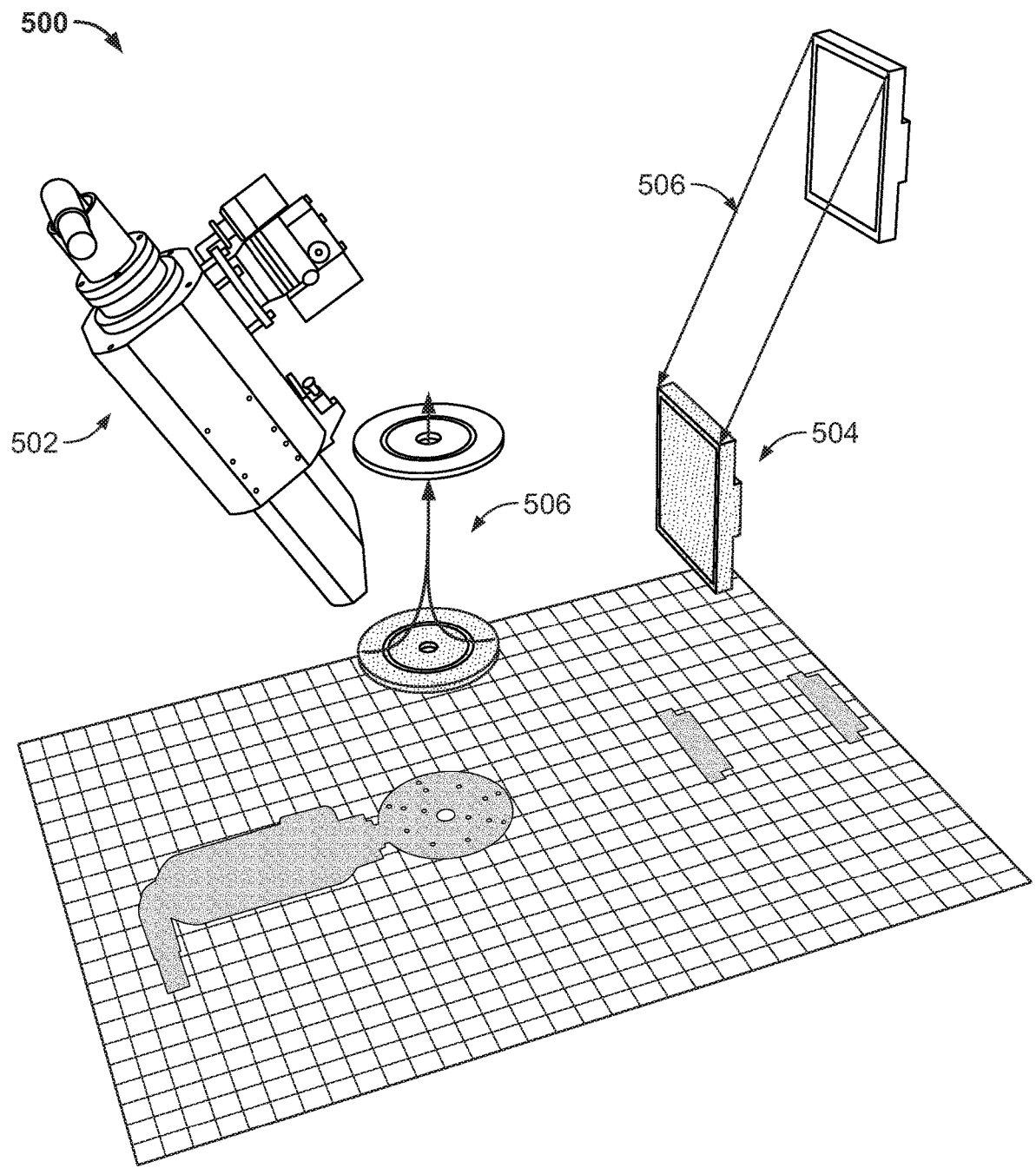
FIG. 5 illustrates an example interface that may be used to implement the scanner positioning control system, showing a first visual representation of a current arrangement of one or more components of the X-ray scanning system, a second arrangement representative of a change to the current arrangement of the one or more components, and an example trajectory between the first arrangement and the second arrangement.

FIG. 5 illustrates an example interface 500 that may be used to implement the scanner positioning control system 200, showing a first visual representation of a current arrangement 502 of one or more components of the X-ray scanning system, a second visual representation of an updated arrangement 504 of the one or more components, and an example trajectory 506 between the first arrangement and the second arrangement.

The example scanner positioning control system 200 may identify a trajectory to be followed by the X-ray emitter 104, the X-ray detector 106, the workpiece positioner 110, and/or any other components in the interface 500 between the current arrangement 502 and the updated arrangement 504. The trajectory 506 may be implemented while moving the components from the current arrangement 502 to the updated arrangement 504 and/or during a scanning operation. The scanner positioning control system 200 outputs a visual representation of the trajectory 506 on the interface 500, which enables an operator to more easily determine whether the desired trajectory will be implemented, as well as to more easily identify whether a collision could occur between components following the trajectory 506.

In some examples, the scanner positioning control system 200 enables the operator to adjust all or part of the trajectory, and/or to require use of a different path-finding techniques by the scanner positioning control system 200 to calculate the trajectory 506.

Particularly when the trajectory 506 is not linear, the example scanner positioning control system 200 may adapt the control of the actuators 116, 118, 120 to implement the desired trajectory. For example, rather than commanding an updated position to be implemented by the PLC 202, the example scanner positioning control system 200 may break down the actuation into multiple, piecewise actuation, for implementation in the X-ray scanning system 100.

Additionally or alternatively, in some examples, the scanner positioning control system 200 may include intermediate arrangement occurring temporally between the current arrangement 502 and the updated arrangement 504, and/or a sequence of states including the current arrangement 502 and multiple updated arrangements. Such intermediate arrangements and/or sequences of arrangements may be useful to the operator to visualize and control complex sequences of arrangements of the components, which may involve multiple movement directions and/or rotation directions, different components moving at different times, and/or any other changes.

Figure 6:
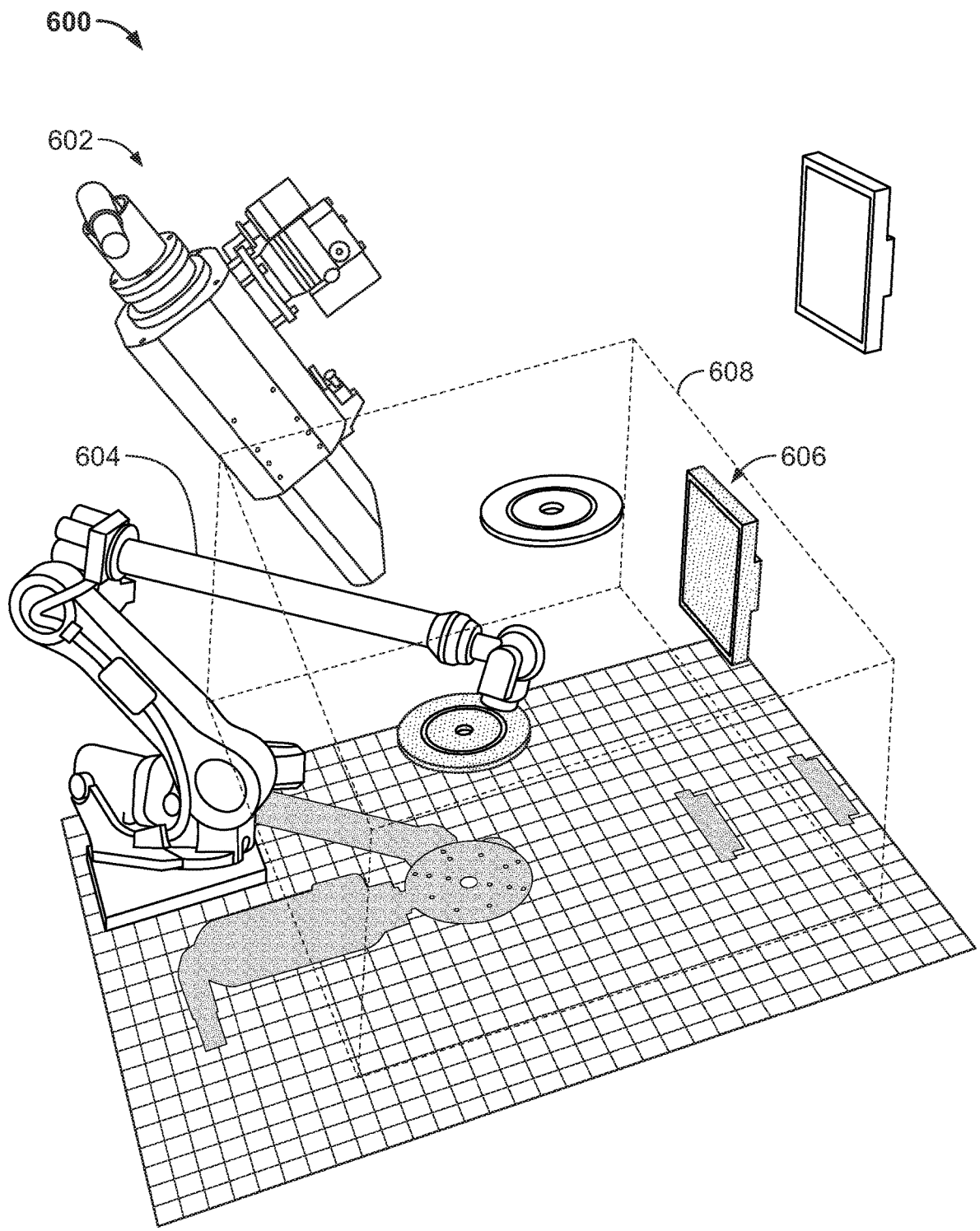
FIG. 6 illustrates an example interface that may be used to implement the scanner positioning control system, showing a first visual representation of a current arrangement of one or more components of the X-ray scanning system including a robotic manipulator, and a second arrangement representative of a change to the current arrangement of the one or more components.

FIG. 6 illustrates an example interface 600 that may be used to implement the scanner positioning control system 200, showing a first visual representation of a current arrangement 602 of one or more components of the X-ray scanning system 100 including a robotic manipulator 604 to implement the workpiece positioner 110, and a second visual representation of an updated arrangement 606 of the one or more components. As in the examples above, the interface 600 may display trajectories of the robotic manipulator 604, ranges of motion of the robotic manipulator 604, projections of the positions of the robotic manipulator 604 onto one or more reference planes, and/or intermediate arrangements and/or sequences of arrangements involving the robotic manipulator 604.

Additionally or alternatively, the scanner positioning control system 200 may display an origin point or configuration of the robotic manipulator 604 on the interface 600 to enable an operator to have a reference point from which to determine the position of the robotic manipulator 604. As with the current arrangement 602 and/or the updated arrangement 606, the example scanner positioning control system 200 may display a projection of the origin configuration onto one or more reference planes. The original configuration may further involve a workpiece being held and manipulated by the robotic manipulator 604.

In some examples, the scanner positioning control system 200 may determine and display range of motion limits 608 of one or more joints of a 6DOF robotic manipulator. In some examples, the scanner positioning control system 200 may enable the operator to manipulate the range of motion limits 608, which causes the scanner positioning control system 200 to constrain the motion of the robotic manipulator 604 when implementing the change from the current arrangement 602 to the updated arrangement 606.

If the scanner positioning control system 200 determines that a motion associated with the change from the current arrangement 602 to the updated arrangement 606 will cause any of the X-ray emitter 104, the X-ray detector 106, the workpiece positioner 110, and/or any other components to exceed the limits of the range of motion (e.g., the range of motion limits 608), the example scanner positioning control system 200 may attempt to calculate a different trajectory from the current arrangement 602 to the updated arrangement 606 that does not exceed the range of motion limits 608, and/or advise the operator that the range of motion limits 608 will be exceeded.

When performing testing, the example scanner positioning control system 200 may store positioning information associated with a captured scan image. The stored positioning information may include similar information as used to generate and display the current arrangements. The positioning information may later be used to visually represent the arrangement of the X-ray emitter 104, the X-ray detector 106, the workpiece positioner 110, the workpiece 108, and/or any other components when the image was captured, such as on the display 208. Additionally or alternatively, the example scanner positioning control system 200 may store and retrieve recipes involving sequences of arrangements for a scanning process, which may also be visualized in a similar manner as the current arrangements, updated arrangements, and/or sequences of arrangements disclosed herein.

Figure 7:
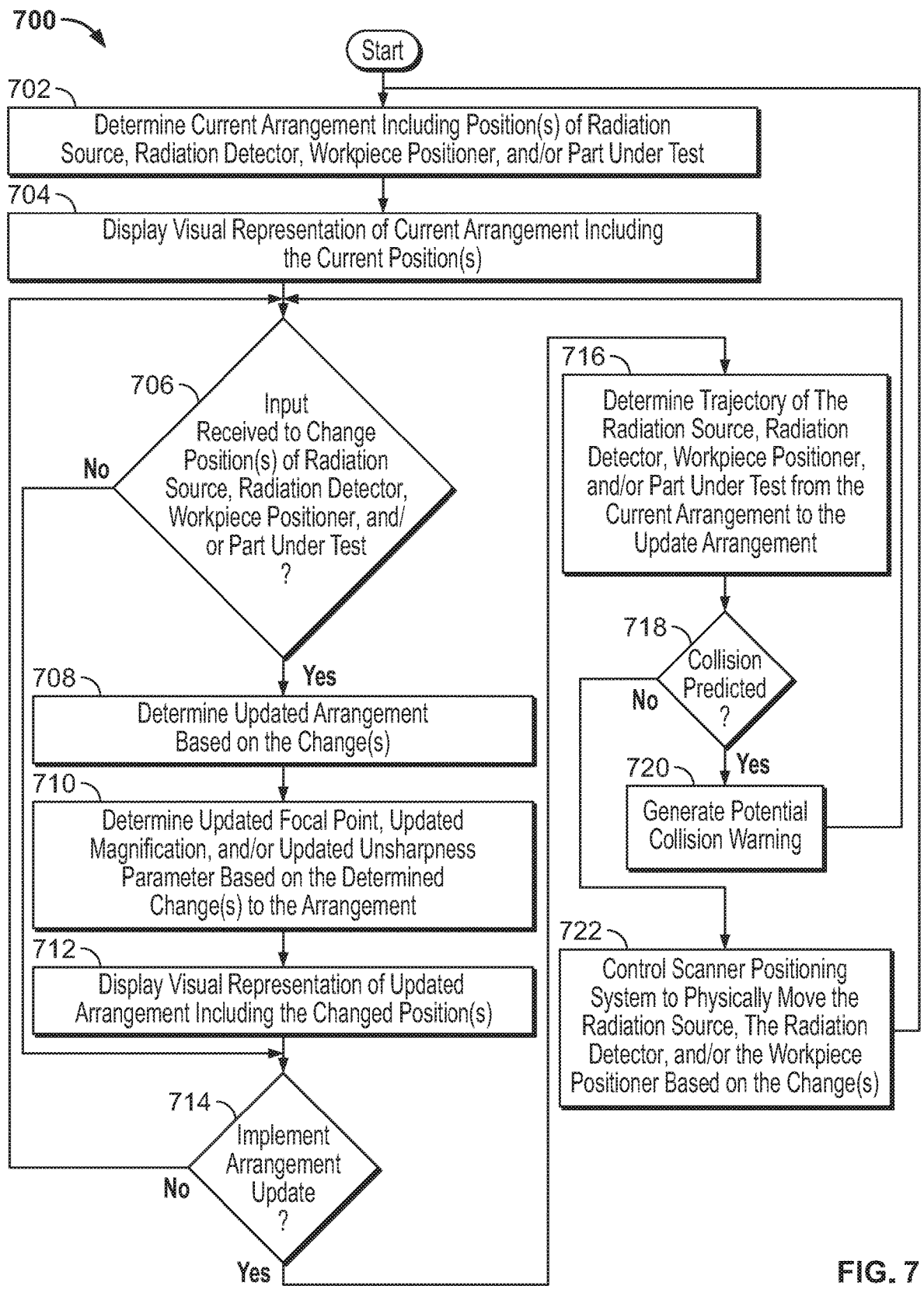
FIG. 7 is a flowchart representative of example machine readable instructions which may be executed by the example computing device of FIG. 2 to perform digital X-ray imaging, in accordance with aspects of this disclosure.

FIG. 7 is a flowchart representative of example machine readable instructions 700 which may be executed by the example scanner positioning control system 200 of FIG. 2 to perform digital X-ray imaging. The example instructions 700 may be performed by the example processor(s) 204 and/or stored as instructions in the memory 206 and/or other storage device(s).

At block 702, the scanner positioning control system 200 determines a current arrangement including position(s) of a radiation source (e.g., the X-ray emitter 104), a radiation detector (e.g., the X-ray detector 106), a workpiece positioner (e.g., the workpiece positioner 110), and/or a part under test (e.g., the workpiece 108). For example, the scanner positioning control system 200 may receive or access position measurements from the position sensor(s) 122 of FIG. 2, and/or monitor the position based on position changes from known or origin position(s) of the X-ray emitter 104, the X-ray detector 106, and the workpiece positioner 110.

At block 704, the scanner positioning control system 200 displays a visual representation of a current arrangement (e.g., the current arrangement 302 of FIG. 3) including the current positions of the X-ray emitter 104, the X-ray detector 106, the workpiece positioner 110, and/or the workpiece 108. For example, the scanner positioning control system 200 may display, via the display 208, the components 304*a*, 306*a*, 308*a* in the interface 300.

At block 706, the scanner positioning control system 200 determines whether inputs have been received to change position(s) of the X-ray emitter 104, the X-ray detector 106, the workpiece positioner 110, and/or the workpiece 108. For example, the scanner positioning control system 200 may receive one or more inputs from the input device(s) 212 to move the components 304*a*, 306*a*, 308*a* in the interface 300. Additionally or alternatively, the input(s) may change updated positions (e.g., the updated components 306*b*, 308*b*) that have not yet been implemented, instead of acting on current positions of the components 304*a*, 306*a*, 308*a*.

If inputs have been received to change position(s) (block 706), at block 708 the scanner positioning control system 200 determines an updated arrangement based on the change (s). For example, the scanner positioning control system 200 may determine a changed position(s) of the X-ray emitter 104, the X-ray detector 106, the workpiece positioner 110, and/or the workpiece 108, and/or projections of the components onto a reference plane 314.

At block 710, the scanner positioning control system 200 determines an update focal point, updated magnification, and/or an updated unsharpness parameter based on the determined change(s) to the current arrangement.

At block 712, the scanner positioning control system 200 displays a visual representation of an updated arrangement (e.g., the updated arrangement 310) including the changed position(s), such as the updated components 306*b*, 308*b*.

After displaying the visual representation of the updated arrangement (block 712), and/or if inputs to change the position(s) have not been received (block 706), at block 714 the scanner positioning control system 200 determines whether to implement the update(s) to the current arrangement 302. For example, the scanner positioning control system 200 may determine whether a command has been received via the input device(s) 212 to implement the changed position(s). If the update is not to be implemented (block 712), control returns to block 706 to await changes to the current and/or updated arrangements.

When the update is to be implemented (block 712), at block 716 the scanner positioning control system 200 determines a trajectory of the X-ray emitter 104, the X-ray detector 106, the workpiece positioner 110, and/or the workpiece 108 from the current arrangement 302 to the updated arrangement 310. For example, the scanner positioning control system 200 may determine one or more paths to travel between the component positions of the current arrangement 302 (e.g., based on the determined positions) and the component positions of the updated arrangement 310 (e.g., based on the commanded positions), as well as actuation paths stored by the scanner positioning control system 200.

At block 718, the scanner positioning control system 200 determines whether a collision is predicted based on the determined trajectory. For example, the scanner positioning control system 200 may monitor the trajectories for potential collisions involving the X-ray emitter 104, the X-ray detector 106, the workpiece positioner 110, the workpiece 108, the enclosure, the door, and/or any other components in the system 100.

If a collision is predicted (block 718), at block 720 the scanner positioning control system 200 generates a potential collision warning and does not implement the update to the arrangement. In some other examples, the scanner positioning control system 200 may attempt to calculate alternative trajectories and/or sequences of actuation to implement the updated arrangement. Control returns to block 706 to permit the operator to provide input(s) to change the updated arrangement so as to avoid collision.

If a collision is not predicted (block 718), at block 722 the scanner positioning control system 200 controls the scanner positioning system (e.g., the actuators 116-120, the PLC 202) to physically move the X-ray emitter 104, the X-ray detector 106, and/or the workpiece positioner 110 based on the change(s). For example, the scanner positioning control system 200 may directly control the actuator(s) 116-120, control the actuator(s) 116-120 via the PLC 202, and/or provide the updated positions to the PLC 202 to permit the PLC 202 to implement the changes. Control returns to block 702 to calculate and display a new current arrangement.

Figure 8:
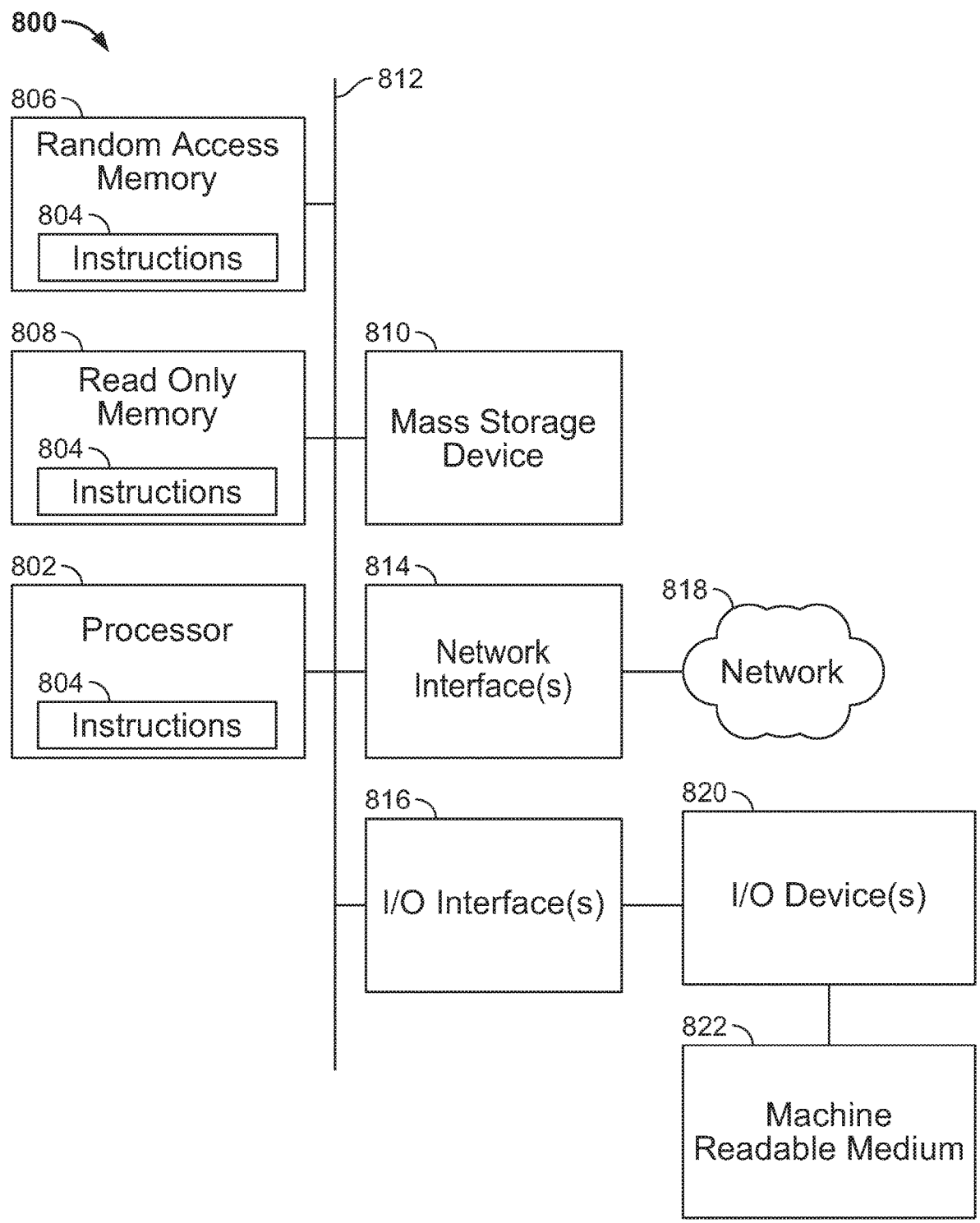
FIG. 8 is a block diagram of an example computing system that may be used to implement the scanner positioning control system of FIG. 2.

FIG. 8 is a block diagram of an example computing system 800 that may be used to implement the scanner positioning control system 200 of FIG. 2. The example computing system 800 may be implemented using a personal computer, a server, a smartphone, a laptop computer, a workstation, a tablet computer, and/or any other type of computing device.

The example computing system 800 of FIG. 8 includes a processor 802. The example processor 802 may be any general purpose central processing unit (CPU) from any manufacturer. In some other examples, the processor 802 may include one or more specialized processing units, such as RISC processors with an ARM core, graphic processing units, digital signal processors, and/or system-on-chips (SoC). The processor 802 executes machine readable instructions 804 that may be stored locally at the processor (e.g., in an included cache or SoC), in a random access memory 806 (or other volatile memory), in a read only memory 808 (or other non-volatile memory such as FLASH memory), and/or in a mass storage device 810. The example mass storage device 810 may be a hard drive, a solid state storage drive, a hybrid drive, a RAID array, and/or any other mass data storage device.

A bus 812 enables communications between the processor 802, the RAM 806, the ROM 808, the mass storage device 810, a network interface 814, and/or an input/output interface 816.

The example network interface 814 includes hardware, firmware, and/or software to connect the computing system 800 to a communications network 818 such as the Internet. For example, the network interface 814 may include IEEE 802.X-compliant wireless and/or wired communications hardware for transmitting and/or receiving communications.

The example I/O interface 816 of FIG. 8 includes hardware, firmware, and/or software to connect one or more input/output devices 820 to the processor 802 for providing input to the processor 802 and/or providing output from the processor 802. For example, the I/O interface 816 may include a graphics processing unit for interfacing with a display device, a universal serial bus port for interfacing with one or more USB-compliant devices, a FireWire, a field bus, and/or any other type of interface. Example I/O device(s) 820 may include a keyboard, a keypad, a mouse, a trackball, a pointing device, a microphone, an audio speaker, an optical media drive, a multi-touch touch screen, a gesture recognition interface, a display device (e.g., the display device(s) 118, 212) a magnetic media drive, and/or any other type of input and/or output device.

The example computing system 800 may access a non-transitory machine readable medium 822 via the I/O interface 816 and/or the I/O device(s) 820. Examples of the machine readable medium 822 of FIG. 8 include optical discs (e.g., compact discs (CDs), digital versatile/video discs (DVDs), Blu-ray discs, etc.), magnetic media (e.g., floppy disks), portable storage media (e.g., portable flash drives, secure digital (SD) cards, etc.), and/or any other type of removable and/or installed machine readable media.

Example wireless interfaces, protocols, and/or standards that may be supported and/or used by the network interface(s) 814 and/or the I/O interface(s) 816, include wireless personal area network (WPAN) protocols, such as Bluetooth (IEEE 802.15); near field communication (NFC) standards; wireless local area network (WLAN) protocols, such as WiFi (IEEE 802.11); cellular standards, such as 2G/2G+ (e.g., GSM/GPRS/EDGE, and IS-95 or cdmaOne) and/or 2G/2G+(e.g., CDMA2000, UMTS, and HSPA); 4G standards, such as WiMAX (IEEE 802.16) and LTE; Ultra-Wideband (UWB); etc. Example wired interfaces, protocols, and/or standards that may be supported and/or used by the network interface(s) 814 and/or the I/O interface(s) 816, such as to communicate with the display device(s) 212, include comprise Ethernet (IEEE 802.3), Fiber Distributed Data Interface (FDDI), Integrated Services Digital Network (ISDN), cable television and/or internet (ATSC, DVB-C, DOCSIS), Universal Serial Bus (USB) based interfaces, etc.

The processor 802, the network interface(s) 814, and/or the I/O interface(s) 816 may perform signal processing operations such as, for example, filtering, amplification, analog-to-digital conversion and/or digital-to-analog conversion, up-conversion/down-conversion of baseband signals, encoding/decoding, encryption/decryption, modulation/demodulation, and/or any other appropriate signal processing.

The computing system 800 may use one or more antennas for wireless communications and/or one or more wired port(s) for wired communications. The antenna(s) may be any type of antenna (e.g., directional antennas, omnidirectional antennas, multi-input multi-output (MIMO) antennas, etc.) suited for the frequencies, power levels, diversity, and/or other parameters required for the wireless interfaces and/or protocols used to communicate. The port(s) may include any type of connectors suited for the communications over wired interfaces/protocols supported by the computing system 800. For example, the port(s) may include an Ethernet over twisted pair port, a USB port, an HDMI port, a passive optical network (PON) port, and/or any other suitable port for interfacing with a wired or optical cable.

The present methods and systems may be realized in hardware, software, and/or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. For example, block and/or components of disclosed examples may be combined, divided, re-arranged, and/or otherwise modified. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed is:

1. A scanner positioning control system, comprising:
a display;
a processor; and
a computer readable storage medium comprising computer readable instructions which, when executed, cause the processor to:
output, via the display, a first visual representation of an arrangement of a radiation source, a radiation detector, and a workpiece positioner;
identify a change to be made to the arrangement of at least one of the radiation source, the radiation detector, or the workpiece positioner;
output, via the display, a second visual representation of the arrangement of the radiation source, the radiation detector, and the workpiece positioner based on the change to be made to the arrangement; and
control a scanner positioning system to physically move the at least one of the radiation source, the radiation detector, and the workpiece positioner based on the change.

2. The scanner positioning control system as defined in claim 1, wherein the first visual representation comprises at least one of: a projection of a current position of the radiation source onto a reference plane; a projection of a current position of the radiation detector onto the reference plane; a projection of a current position of the workpiece positioner onto the reference plane; or a projection of a part positioned on the workpiece positioner onto the radiation detector based on the current position of the radiation source, the radiation detector, and the workpiece positioner.

3. The scanner positioning control system as defined in claim 1, wherein the second visual representation comprises at least one of: a projection of a changed position of the radiation source onto the reference plane based on the change to be made to the arrangement; a projection of a changed position of the radiation detector onto the reference plane based on the change to be made to the arrangement; a projection of a changed position of the workpiece positioner onto the reference plane based on the change to be made to the arrangement; or a projection of the part positioned on the workpiece positioner onto the radiation detector based on the change to be made to the arrangement.

4. The scanner positioning control system as defined in claim 1, wherein the computer readable instructions cause the processor to control the scanner positioning system by controlling at least one of: an enclosure in which the radiation source, the radiation detector, and the workpiece positioner are enclosed; a door of the enclosure; boundaries of the enclosure; a limit of motion of at least one of radiation source, the radiation detector, or the workpiece positioner; a range of motion in which a collision involving at least one of radiation source, the radiation detector, or the workpiece positioner has less than a threshold likelihood of occurring; a filter wheel; a collimator; or a shutter.

5. The scanner positioning control system as defined in claim 1, wherein the computer readable instructions cause the processor to access current positions of the radiation source, the radiation detector, and the workpiece positioner, and determine the first visual representation of the arrangement of the radiation source, the radiation detector, and the workpiece positioner based on the positions.

6. The scanner positioning control system as defined in claim 1, wherein the first visual representation comprises at least one of a representation of a current focal point of radiation emitted by the radiation source or an updated focal point based on the change to be made to the arrangement.

7. The scanner positioning control system as defined in claim 1, wherein the computer readable instructions cause the processor to determine at least one of a magnification, an unsharpness parameter, or a focal length of the radiation detector following the change to be made to the arrangement.

8. The scanner positioning system as defined in claim 1, wherein the computer readable instructions cause the processor to:
identify a trajectory to be followed by at least one of the radiation source, the radiation detector, or the workpiece positioner during a scanning operation, the trajectory having a starting arrangement of the radiation source, the radiation detector, and the workpiece positioner and an ending arrangement of the radiation source, the radiation detector, and the workpiece positioner;
output, via the display, a third visual representation comprising the starting arrangement and the ending arrangement; and
control the scanner positioning system during the scanning operation to physically move the at least one of the radiation source, the radiation detector, and the workpiece positioner based on the trajectory from the starting arrangement to the ending arrangement.

9. The scanner positioning system as defined in claim 8, wherein the third visual representation visually represents at least one of a change in position or a change in orientation of at least one of the radiation source, the radiation detector, and the workpiece positioner between the starting arrangement and the ending arrangement.

10. The scanner positioning system as defined in claim 1, wherein the first visual representation and the second visual representation are three-dimensional representations.

11. The scanner positioning system as defined in claim 1, wherein the computer readable instructions cause the processor to determine a range of motion of at least one of the radiation source, the radiation detector, or the workpiece positioner, wherein at least one of the first visual representation or the second visual representation include a representation of the range.

12. The scanner positioning system as defined in claim 11, wherein the computer readable instructions cause the processor to determine whether a motion associated with the change to the arrangement will cause at least one of the radiation source, the radiation detector, or the workpiece positioner to exceed the limits of the range of motion.

13. The scanner positioning system as defined in claim 1, wherein at least one of the first visual representation or the second visual representation includes a representation of a workpiece held on the workpiece positioner.

14. The scanner positioning system as defined in claim 1, wherein at least one of the first visual representation or the second visual representation comprises a representation of a robot arm, an origin point of a movement of the workpiece positioner, or one or more vectors representative of the change to the arrangement.

15. The scanner positioning system as defined in claim 1, wherein the computer readable instructions are to cause the processor to output, via the display, a third visual representation of an intermediate arrangement of the radiation source, the radiation detector, and the workpiece positioner based on the arrangement and the change to be made to the arrangement.

16. The scanner positioning system as defined in claim 1, wherein at least one of the first visual representation or the second visual representation comprises at least one of an enclosure, an enclosure door, a filter wheel, a radiation source collimator, or a radiation source shutter.

17. The scanner positioning system as defined in claim 1, wherein the computer readable instructions cause the processor to determine at least one of a magnification, an unsharpness parameter, or a focal length of the radiation detector of the arrangement.

18. The scanner positioning system as defined in claim 1, further comprising a user input device, wherein the computer readable instructions cause the processor to identify the change to be made to the arrangement based on one or more inputs via the user input device.

19. A scanner positioning system, comprising:
a display;
a processor; and
a computer readable storage medium comprising computer readable instructions which, when executed, cause the processor to:
render a three-dimensional representation of a radiation source, a radiation detector, and a workpiece positioner based on an arrangement of the radiation source, the radiation detector, and the workpiece positioner;
render changes to the arrangement in response to commands to change the arrangement; and
control positions and orientations of the radiation source, the radiation detector, and the workpiece positioner based on the rendered arrangement including the rendered changes.

20. A scanner positioning control system, comprising:
a display;
a processor; and
a computer readable storage medium comprising computer readable instructions which, when executed, cause the processor to:
output, via the display, a first visual representation of a first state of a radiation source, a radiation detector, and a workpiece positioner;
identify a change to be made to the first state based on a modeled manipulation of the first visual representation;
output, via the display, a second visual representation of a second state of the radiation source, the radiation detector reflecting the modeled manipulation; and
control a scanner positioning system to physically move the at least one of the radiation source, the radiation detector, and the workpiece positioner to positions represented in the second state.

* * * * *